United States Patent
Conrady

(10) Patent No.: US 8,089,057 B2
(45) Date of Patent: Jan. 3, 2012

(54) RADIATION CONVERTER AND IRRADIATION ARRANGEMENT CONTAINING SAID CONVERTER

(75) Inventor: Jürgen Conrady, Berlin (DE)

(73) Assignee: Spectrometrix Optoelectronic Systems GmbH, Berlin (DE)

( * ) Notice: Subject to any disclaimer, the term of this patent is extended or adjusted under 35 U.S.C. 154(b) by 1613 days.

(21) Appl. No.: 10/577,207

(22) PCT Filed: Oct. 26, 2004

(86) PCT No.: PCT/EP2004/012240
§ 371 (c)(1),
(2), (4) Date: Apr. 26, 2006

(87) PCT Pub. No.: WO2008/042100
PCT Pub. Date: May 12, 2005

(65) Prior Publication Data
US 2007/0145336 A1 Jun. 28, 2007

(30) Foreign Application Priority Data
Nov. 3, 2003 (DE) .................................. 103 51 706

(51) Int. Cl.
*A61N 5/06* (2006.01)
(52) U.S. Cl. ............... 250/504 R; 250/458.1; 250/459.1; 250/461.1; 607/88; 607/90; 607/94
(58) Field of Classification Search ............... 250/458.1, 250/459.1, 461.1, 504 R; 607/88, 90, 94
See application file for complete search history.

(56) References Cited

U.S. PATENT DOCUMENTS
4,371,897 A * 2/1983 Kramer .......................... 358/474
(Continued)

FOREIGN PATENT DOCUMENTS
DE 29 10 468 A1 9/1980
(Continued)

OTHER PUBLICATIONS
"Opinion on Quality Assurance in UVA1 Phototherapy, Version of the Photo(chemo)therapy and -diagnosis Subgroup of the Subcommittee on Physical Methods in Dermatology, May 1998" May 1998.
(Continued)

*Primary Examiner* — Michael Maskell
(74) *Attorney, Agent, or Firm* — Frank J. Bonini, Jr.; John F. A. Earley, III; Harding, Earley, Follmer & Frailey, P.C.

(57) ABSTRACT

Light therapy in the visible spectral region, for which radiation sources emitting UV radiation are provided, uses fluorescent films that age during operation such that the intensity of the light irradiated by the fluorescent films gradually decreases. In order to solve this problem, the invention relates to a radiation converter located in a treatment device and comprising a fluorescent layer (2) for emitting the visible light. Said radiation converter comprises a housing (1) that can be penetrated by radiation emitted by the radiation source (11). The housing (1) comprises a front wall (3) consisting of a UV-permeable material and a rear wall (4) consisting of a UV-impermeable material, on the side of the housing (1) opposing the front wall (3). A liquid chamber (5) is formed between the front wall (3) and the rear wall (4), and the fluorescent layer (2) is arranged between the front wall (3) and the rear wall (4).

20 Claims, 2 Drawing Sheets

U.S. PATENT DOCUMENTS

Figure 1A:
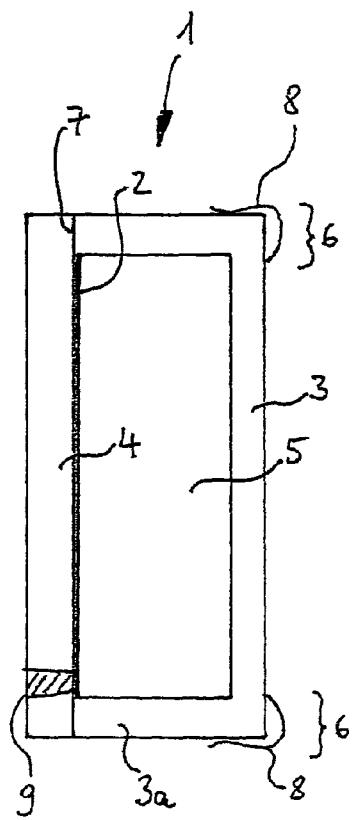

| | | | |
|---|---|---|---|
| 6,447,537 B1* | 9/2002 | Hartman | 607/94 |
| 7,891,361 B2* | 2/2011 | Irwin | 128/898 |
| 2002/0161418 A1 | 10/2002 | Wilkens et al. | |
| 2003/0004501 A1 | 1/2003 | Wilkens et al. | |

FOREIGN PATENT DOCUMENTS

| | | |
|---|---|---|
| DE | 101 23 926 A1 | 9/2002 |
| EP | 0 016 870 A1 | 10/1980 |
| EP | 0 164 663 A2 | 12/1985 |
| EP | 0 592 794 A2 | 4/1994 |
| WO | WO 01/21728 A1 | 3/2001 |
| WO | WO 01/97912 A2 | 12/2001 |
| WO | WO 02/14388 A1 | 2/2002 |

OTHER PUBLICATIONS

"Guidelines for Quality Assurance in Photo(chemo)therapy and -diagnosis" Sep. 1997 Handbuch der Dermatologischen Phototherapie and -Diagnostic, Springer-Verlag, Heidelberg, pp. 392-395.

* cited by examiner

RADIATION CONVERTER AND IRRADIATION ARRANGEMENT CONTAINING SAID CONVERTER

The present invention pertains to a radiation converter and an irradiation arrangement containing the converter. The irradiation arrangement is used especially for the long-term treatment of fully or partially cell-mediated inflammations of the skin and the inner organs, viral and other infectious diseases, for example, prion infections, above all for the treatment of T-cell-mediated skin diseases and eczemas of the hand.

Primarily T-cell-mediated skin diseases, for example, atopic dermatitis (neurodermatitis), cutaneous T-cell lymphoma, lichen ruber and psoriasis, are based on a skin infiltrate of activated T lymphocytes intrinsic to the body. Ever-increasing numbers of newborns and children are affected especially by neurodermatitis. This disease represents a severe stress both physiologically and psychologically because of the inflamed skin parts as well as the pruritus associated with it.

The therapies known hitherto for the treatment of neurodermatitis can be classified essentially to two cases, namely, chemotherapy and UVA1 phototherapy.

In chemotherapy, glucocorticoid therapy is currently the gold standard in the therapy of atopic dermatitis. This therapy involves both systemic and topical use and there are sometimes severe side effects. Alternative methods for the therapy of neurodermatitis include the therapy with strongly immunomodulating drugs, for example, with FK 506 or cyclosporin A, about whose long-term consequences there is no experience so far.

UVA1 phototherapy has proved to be effective in the treatment of acute attacks of neurodermatitis, urticaria pigmentosa and localized scleroderma. Two types of devices are currently offered for UVA1 therapy according to Meffert and for UVA1 therapy according to Krutmann. The UVA1 therapy according to Meffert operates with broad band between 340 nm and 500 nm, and the UVA1 therapy according to Krutmann at 340-400 nm.

A very good review of the state of the art of UVA1 therapy can be found in "Opinion on Quality Assurance in UVA1 Phototherapy, Version of the Photo(chemo)therapy and -diagnosis Subgroup of the Subcommittee on Physical Methods in Dermatology, May 1992" as well as in the "Guidelines for Quality Assurance in Photo(chemo)therapy and -diagnosis," which was published in Krutmann, S. and H. Hönigsmann: *Handbuch der Dermatologischen Phototherapie und -Diagnostik*, Springer-Verlag, Heidelberg, pp. 392-395. Premature aging of the skin and carcinogenicity are mentioned there as long-term risks. Based on these facts, it is explicitly stated there that the use of medium and high doses of UVA1 in childhood is not to be recommended. However, precisely the largest affected group of patients with neurodermatitis is thus excepted.

Two types of DNA damage, namely, the production of pyrimidine dimers and oxidative DNA modifications, occur during irradiation. The first group of DNA damage is comparatively difficult to repair by means of ondogenous repair enzymes, and the induction of such damage is carcinogenic. The maximum of this damage is induced by irradiation with a wavelength of about 290 nm, the degree of damage being lower at 400 nm by a factor of 10,000 and being no longer detectable at wavelengths above 425 nm. This type of damage is also called CPD (cyclobutane pyrimidine photodimers).

The type of the so-called indirect DNA damage, which is presumably brought about via the photoexcitation of cellular chromophores, differs from this. These chromophores produce reactive oxygen species, for example, singlet oxygen. A DNA damage (8-hydroxyguanine) induced hereby is repaired by the so-called FPG protein endonuclease. This is comparatively minor damage in the region of the DNA crosslink rather than DNA strand breaks or base loss. This was demonstrated by experiments with transgenic mice without FPG repair enzymes, which nevertheless failed to show increased tumor rates.

Photobiological effects in the non-UV range based on an interaction between endogenous or exogenous chromophores in the skin are of increasing significance because therapeutic effects can be affected by means of suitable radiation sources in certain inflammatory skin diseases and, e.g., disturbances in wound healing in diabetes mellitus.

A radiation converter with a radiation source for two-dimensional irradiation of the area to be treated is described in DE 101 23 926 A1 for the treatment of acute and chronic, fully or partially cell-mediated inflammations of the skin and the inner organs, of viral and other infectious diseases such as HIV or prion diseases, fungal infections of the skin and mucosa, bacterial diseases of the skin and mucosa as well as hand and anal eczemas. The wavelength of the emitted radiation on the area being treated is greater than 400 nm and comprises a spectral range in the wavelength range of 400-500 nm. The irradiation arrangement comprises means for generating optical pulses on the area being treated, the intensity of irradiation of the irradiation peaks of the optical pulses being greater than 1 W/cm$^2$ and lower than 100 kW/cm$^2$. A commercially available Xe flash lamp is used as the radiation source.

The radiation emitted by the flash lamp is typically in the range of 200 to 2,000 nm. To prevent the undesired UV radiation from reaching the body parts to be treated, these spectral ranges can be filtered out by means of commercially available filters. However, it is also proposed in the document that the UV components be transformed into the desired spectral range. Especially films with inorganic fluorescent material, which films consist of silicone elastomers, have proved be to suitable for this purpose.

The manufacture of such a silicone elastomer film is described in WO 01/21728 A1. According to data in this document, silicone elastomers are better than acrylates, transparent PVC or Teflon® (DuPont), because the latter lack sufficient thermal stability, whereas the silicone elastomers are stable at temperatures of up to 250° C. Moreover, the latter require no plasticizing agents or other volatile substances, which could evaporate. Especially the free radical addition polymerization technique is used to manufacture the silicone elastomer. The elastomer is preferably formed from a hydroxypolydiorganosiloxane and an organohydrogen siloxane in the presence of a platinum catalyst at room temperature. The film can be arranged, in particular, on the outer side of the enveloping body of the low-pressure discharge lamp, for example, by mounting the film in the form of a changing frame on the enveloping body or wrapping the film around the body part to be treated in the manner of a bandage. In the first case, the film may be stored on rollers in such a way that it can be wound up and unwound, so that an unused part of the fluorescent layer is available for therapeutic application should the fluorescent material contained in the unwound area be aged. The used fluorescent film is wound up before the treatment in this case.

However, the measure of winding up the fluorescent film on a roller when it is aged by the irradiation is disadvantageous because a large amount of film is needed for this and because the feeding and the removal of the film with the rollers requires solutions involving a great design effort.

Therefore, the basic object of the present invention is to avoid or at least reduce the aging of the film.

This object is accomplished by the radiation converter according to claim 1 and the irradiation arrangement according to claim 18. Preferred embodiments of the present invention are described in the subclaims.

The radiation converter according to the present invention is used especially in conjunction with a UV-emitting radiation source in an irradiation arrangement according to the present invention. Light is generated in the visible range, whose wavelength is in the blue, yellow, green or red color range depending on the discharge lamp used and depending on the radiation converter, by fluorescence or phosphorescence by the UV component in the radiation of the radiation source, which is absorbed in the radiation converter. The irradiation arrangement is preferably formed such that light with a large spectral component in the blue range is emitted by the radiation converter.

The radiation may be emitted especially in light pulses. Mainly medium-pressure and high-pressure lamps operated in pulse overload, for example, mercury iodide lamps, or a high-pressure Xe flash lamp, may be used for this purpose, in particular.

Especially eczemas of the hand and T-cell-mediated skin diseases can be treated with the irradiation arrangement according to the present invention. The latter include above all atopic dermatitis (neurodermatitis), cutaneous T-cell lymphoma, lichen ruber and psoriasis.

The radiation converter according to the present invention has as an essential feature a fluorescent layer, in which the UV radiation emitted by a radiation source, especially a UV-emitting radiation source, is converted into visible, preferably blue light.

It was found that the aging of the fluorescent layer can be retarded or even completely prevented if the fluorescent layer is arranged in a housing that is permeable to radiation that is emitted by the UV-emitting radiation source and has the following features:
 a) a front wall made of UV-permeable material,
 b) a rear wall made of UV-impermeable material on the side of the housing opposite the front wall,
 c) wherein a liquid chamber is formed between the front wall and the rear wall,
 d) the fluorescent layer between the front wall and the rear wall.

An investigation of a radiation converter that has a fluorescent layer consisting of a silicone elastomer with fluorescent material with a UV-emitting radiation source revealed that marked aging effects appear already when the radiation power density reaching the converter, integrated over a wavelength range of 260-1,050 nm, is above 400 mJ/cm$^2$.

For the treatment, the radiation converter is brought into the ray path of the UV-emitting radiation source.

The aging of a fluorescent layer during irradiation with the UV-emitting radiation source turned out to be markedly delayed by the arrangement of the radiation source in the radiation converter according to the present invention. Thus, it is seen that the intensity of the radiation emitted by the layer, for example, of blue light, decreases markedly more slowly than when a fluorescent layer that is not arranged in the radiation converter according to the present invention is used.

The housing of the converter comprises a front wall and a rear wall. The front wall is the wall facing the UV-emitting radiation source, whereas the rear wall is the wall located opposite the front wall in the housing, which faces away from the UV-emitting radiation source. Both the front wall and the rear wall consist of acrylate polymer in a preferred embodiment of the present invention. Among the acrylate polymers, especially polymethyl methacrylates have important advantages, for example, very good optical properties (high transparency in the visible and UV ranges) and thermal properties (high dimensional stability under heat). In addition, they are inexpensive. These materials are usually used for windows in tanning beds and other lighting fixtures, unless very high thermal load-bearing capacity is required, as well as in greenhouses.

Radiation originating from the UV-emitting radiation source is first passed through the UV-permeable front wall in the housing and after passing through the liquid chamber, it reaches the fluorescent layer. If small UV components are still present after the passage of the radiation through the fluorescent layer, these components are absorbed in the UV-impermeable rear wall. UV radiation is thus prevented from reaching the body parts to be treated.

Suitable UV-permeable acrylate materials are disclosed, for example, in EP 0 016 870 A1, EP 0 164 663 A2 and WO 02/14388 A1. Accordingly, UV permeability of the acrylate material, which also persists over a rather long period of time, can be achieved, on the one hand, by the polymerization of the underlying acryl monomer being carried out in the presence of a sterically hindered amine according to formula I given there. Mainly diesters of 2,2,6,6-tetramethyl-piperidyl-4 derivatives of aliphatic dicarboxylic acids, especially di-(2,2,6,6-tetramethyl-piperidyl-4)-sebacate (EP 0 016 870 A1), are suitable for such sterically hindered amines. On the other hand, UV stability can also be imparted to these materials by the plastic additionally containing an aliphatic plasticizer, which is compatible with polymethyl methacrylate and is stable above 120° C. Such plasticizers are, for example, compounds with one or more ester, ether or hydroxyl functional groups, especially diethyl adipate, diethylene glycol monomethyl ether and glycerol triacetate (EP 0 164 663 A2). Finally, a so-called active component may also be added to the polymerization mixture in order to further improve the UV stability. Especially alcohols, water, vinyl compounds or butyl lactate are mentioned as active components (WO 02/14388 A1).

The UV permeability of the rear wall can be achieved by adding a UV absorber to the reaction mixture before the polymerization. Such an absorber may be, for example, part of the polymer skeleton to be prepared by polymerization, for example, styrene, divinyl benzene or another aromatic compound, which can be polymerized with the acryl monomers. Instead of these UV-absorbing skeletal monomers, it is also possible to add other UV-absorbing substances, preferably to the reaction mixture, for example, benzotriazole and benzophenone derivatives.

The acrylate polymer, of which the front wall and the rear wall are manufactured, may be either a homopolymer, a copolymer or a block polymer of acrylate monomers. The acrylate polymers are especially compounds selected from the group comprising alkyl acrylates and alkyl methacrylates. These are especially polymethyl methacrylate as well as the copolymers of methyl methacrylate with alkyl acrylates, especially methyl acrylate and ethyl acrylate.

The fluorescent layer may be introduced into the housing either as a self-supporting film during the assembly or it may be applied as a layer to one of the walls. Since such films are commercially available, the use of a fluorescent film is to be preferred. However, the layer may, in principle, also be formed by an application process on the wall surface before the mounting of the housing, for example, by knife-coating, screen printing, curtain pouring, spin coating or another prior-art method, using a liquid form of the material for the layer, for example, a solution, emulsion or dispersion.

In a preferred embodiment of the present invention, the fluorescent layer is introduced into the housing such that it is in contact with the surface of the rear wall. In this case, the radiation first passes through the front wall and the liquid chamber in the housing during the operation before it reaches the fluorescent layer. However, the fluorescent layer may, in principle, also be introduced into the housing in such a way that it is in contact with the inner side of the front wall. After passing through the front wall, the radiation reaches the layer directly in this case before it passes through the liquid chamber. The fluorescent layer adjoins the liquid chamber in both cases. The alternative in which the layer is introduced into the chamber in such a way that it is in contact with the rear wall has the advantage that the layer will not age as rapidly as in the case in which the fluorescent layer is introduced into the housing in such a way that it is in contact with the front wall. The case in which the layer is designed as a film and is mounted freely hanging in the liquid chamber without being in contact with one of the two walls is conceivable as well. It may be necessary in this case to provide a reinforcing grid, which is in contact with the film either on one side or on both sides and is anchored in the radiation converter in a stable manner and has a good rigidity itself, for the mechanical reinforcement of the film. This grid should cover only a small percentage of the area of the film in order to avoid a marked loss of intensity.

The fluorescent layer preferably consists of a silicone elastomer with incorporated fluorescent particles. Due to the fluorescent layer being designed as a film of silicone elastomer with incorporated fluorescent particles, it is possible, on the one hand, to manufacture films of sufficient thickness with a sufficiently high concentration of fluorescent material. On the other hand, the fluorescent particles are crosslinked in the silicone elastomer without air and water, so that they are not subject to any aging behavior. Because of the hydrophobic character of the silicone elastomers, moisture cannot practically enter these materials, so that the moisture-sensitive fluorescent materials are not damaged.

However, it is, of course, also possible to use other polymers for the fluorescent layer, for example, transparent PVC and polyfluoroalkylenes, especially polytetrafluoroethylene (Teflon®), instead of silicone elastomers.

The silicone elastomer layer is preferably prepared by free radical addition polymerization in the presence of the fluorescent particles to be embedded because, contrary to a polycondensation reaction, practically no harmful byproducts, for example, water, which could compromise the function of the fluorescent particles, are released during an addition polymerization. The starting products for the polymerization are especially hydroxypolydiorganosiloxanes and organohydrogen siloxanes, which are reacted with one another in the presence of a catalyst, while a crosslinked polymerization product is formed. Especially substances with a minimum viscosity of 1,000 cP are used as hydroxypolydiorganosiloxanes from different polymers, these preferably being hydroxypolydimethylsiloxane and copolymers thereof with phenyl dimethylsiloxane and/or polymethyl-3,3,3-trifluoropropylsiloxane. The organohydrogen siloxane contains at least two hydrogen atoms per siloxane unit, and both homopolymers and copolymers can be used in this case as well. The catalyst may be especially a platinum compound, preferably platinum chloride or chloroplatinic acid. By using the platinum catalyst, the polymerization reaction can be carried out at room temperature, so that the fluorescent particles, which are present during the polymerization, are not subject to thermal stress and are not damaged thereby.

The fluorescent particles in the layer are preferably crystalline. A strontium pyrophosphate doped with europium(II) ions ($Sr_2P_2O_7:Eu^{2+}$) proved to be especially suitable. UV radiation can be converted into blue light with this type of fluorescent material. It is possible to use other fluorescent materials to also convert the UV radiation into visible light with a different spectral distribution or for other reasons as well. In an especially suitable embodiment, the fluorescent layer is designed such that it contains different fluorescent particles in different areas. This is advantageous when the patient to be treated is to be irradiated simultaneously with light with different spectral compositions in different areas. Body parts can also be irradiated with such arrangements with light of different spectral distributions in rapid succession.

The fluorescent layer preferably has a thickness in the range of 10 μm to 800 μm, especially preferably 100 μm to 600 μm, the thickness being one of the parameters for optimizing the efficiency of the radiation generation. The efficiency depends essentially on the density by surface of the fluorescent material in the layer. This should be in the range of 1 mg/cm$^2$ to 20 mg/cm$^2$. Densities by surface in the range of 3 mg/cm$^2$ to 6 mg/cm$^2$ are especially advantageous.

The effectiveness of radiation generation is substantially affected by the geometric conditions in the radiation converter: For example, if the walls of the housing are not in the form of flat plates but are curved, only a very low radiation power is reached in the visible range. The cause of this is not known. If the front wall and the rear wall are designed, by contrast, as plates, a substantially improved radiation power is reached. Optimal radiation emission is made possible if the front wall and the rear wall form surfaces that are plane parallel to one another. The thickness of the liquid chamber is preferably in the range of 0.5-5 mm. It especially preferably equals 2 mm.

The liquid chamber in the radiation converter is filled with at least one cooling liquid. Substances that are selected from the group comprising silicone oils and water, where silicone oils have proved to be even more suitable than water, are preferably used as cooling liquids. In case of water as the cooling liquid, the radiation power drops with time during phases of rest, i.e., when no radiation falls on the converter, It was observed that gas bubbles and opacity are formed in the liquid during these phases of rest. To remove the gas bubbles, a viscoelastic area, for example, a rubber plug, may be provided in one of the two walls, the said plug extending through the entire thickness of the said wall. The gas bubbles can then be drawn off with a syringe, which is passed through the plug.

The coordination of the refractive indices of the cooling liquid, the material for the fluorescent layer and the materials for the walls with one another is very important for the intensity of the radiation in the visible range exiting from the radiation converter:

Since the radiation generated in the fluorescent film is emitted isotropically, about half of the radiation is also radiated back in the direction of the UV-emitting radiation source. To reduce this component in favor of the radiation emitted in the direction of the body part to be treated, the refractive indices of the said materials may be coordinated with one another such that at least part of the radiation cannot exit from the fluorescent layer in the direction of the radiation source due to total reflection and a corresponding exit in the direction of the body part is not hindered by total reflection effects. If, for example, the layer is introduced into the housing such that it is in contact with the rear wall, the refractive index of the material of the rear wall should be greater than that of the fluorescent layer and the latter should in turn be greater than that of the cooling liquid. The radiation arriving from the UV-emitting radiation source in this case can enter the cooling liquid through the front wall without problems and it can enter the fluorescent layer from there, because this radiation is directed, so that total reflection at the boundary surfaces between the front wall and the cooling liquid and between the cooling liquid and the fluorescent layer can be reduced by suitably guiding the radiation, especially by irradiating the radiation converter with the UV radiation essentially at right angles.

In the same manner, the refractive indices of the said materials can also be coordinated with one another in a suitable manner when the fluorescent layer is introduced into the housing in such a way that it is contact with the front wall or when the layer is mounted freely hanging in the cooling liquid in the form of a film. The intensity of the radiation exiting from the radiation converter can also be optimized in the latter case by suitably selecting the cooling liquid in the two liquid chambers formed by the film by selecting different liquids with suitable refractive indices in relation to those of the materials of the fluorescent layer and the two walls.

The front wall and the rear wall may be connected with one another in substance for the liquid-tight sealing of the liquid chamber in the two edge areas. For example, one of the two walls may have a marginal edge projection, to which the other wall is attached. The two walls are then connected with one another, for example, bonded, preferably with an acryl adhesive, at the connection surfaces. Depending on the fluorescent layer, this may also extend into the area of the connection surface, so that the two walls are connected with one another via the layer.

To prevent the connection points from being damaged by the radiation, the front wall may be provided with a mask in the marginal areas to shadow the front wall, so that the radiation does not fall directly on the connection points. The mask may be either a protective coating resistant to the radiation, which is impermeable to the radiation, or a masking frame, which is clamped onto the radiation converter housing.

Furthermore, a changing bracket may be provided for the housing. This makes it possible to easily change or replace the housing with a new housing, e.g., when the effectiveness of the fluorescent layer is already compromised by the radiation and the layer must be replaced with another one or when a fluorescent layer with other fluorescent materials is to be used to generate a radiation with another spectral range or with other irradiation intensities. The changing bracket can be advantageously connected directly with the UV-emitting radiation source. As a result, a compact design is obtained. In addition, the converter is arranged as a result in the immediate vicinity of the radiation source, so that the converter may also have a small size, because the radiation cross section is smaller in the vicinity of the radiation source than at a greater distance from it.

It may be advantageous for certain types of treatment to topically rinse the irradiated body parts with oxygen. For the effect of oxygen treatment, reference is also made to DE 101 23 926 A1. As a result, the oxygen content is increased in the body parts to be treated, which in turn increases the production of therapeutically effective reactive $O_2$ species. The radiation converter may have a bell-shaped design at the rear wall for this case. The converter is placed in this case on the body part to be treated, so that a cavity, which can be flooded with oxygen, is formed between the bell-shaped rear wall and the body part. A feed pipe connection for oxygen is provided for this purpose at the bell-shaped rear wall. A highly compact design is also obtained due to this embodiment. If the radiation converter is additionally provided with a cooling circuit for the cooling liquid, the UV-emitting radiation source and the radiation converter of compact design can be placed directly on the body part to be treated via the bell without having to fear that the body part will be damaged by excessive evolution of heat.

Figure 1B:
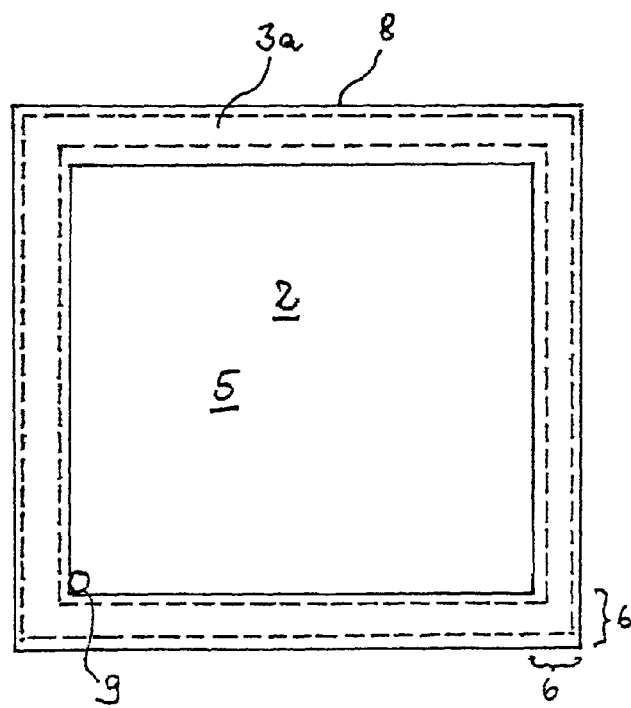
Figure 2:
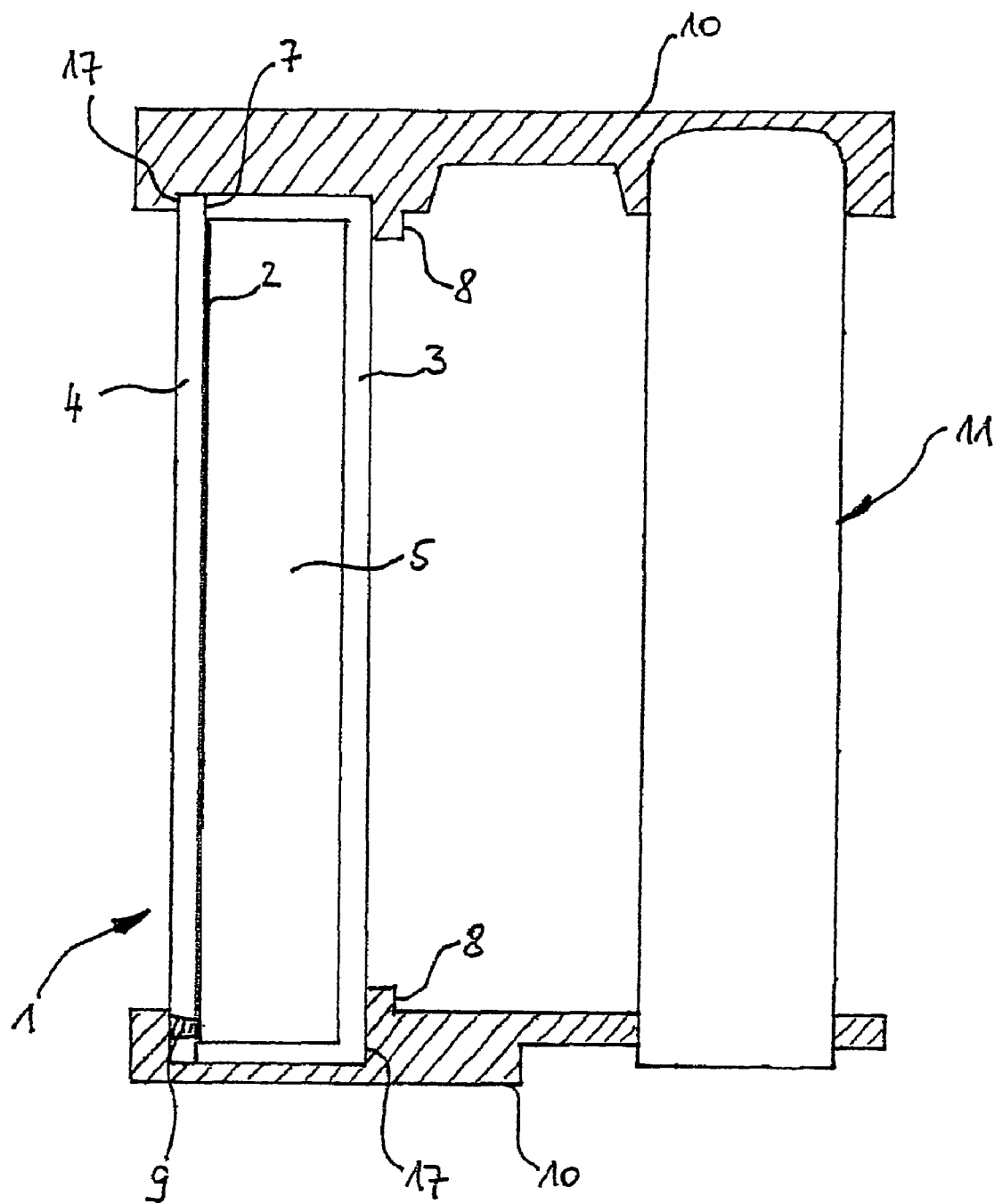

The following figures are to illustrate the present invention. In the drawings,

FIG. 1a shows a sectional side view through the housing of a radiation converter, FIG. 1b shows a top view of the housing of the radiation converter, and FIG. 2 shows a sectional side view through an irradiation arrangement.

FIG. 1a shows a sectional side view through the housing 1 of a radiation converter. FIG. 1b shows a top view of this housing 1. The housing 1 comprises a UV-permeable front wall 3 and a UV-impermeable rear wall 4. The two walls consist of polymethyl methacrylate. In the edge areas 6, the front wall 3 has an edge projection 3a, which ["die sich" in line 15, p. 15 of German original is a typo for "der sich"—Tr.Ed.] extends over all edge areas 6. The front wall 3 lies with the faces of the edge projection 3a on the corresponding edge areas 6 of the rear wall 4. The two walls 3, 4 are bonded to one another there in a liquid-tight and gas-tight manner. A chamber 5 is formed by the connection in substance that is created there at the connection point 7 between the front wall 3 and the rear wall 4. This chamber is filled with silicone oil, for example, with Baysilone® oil M (Bayer).

A fluorescent film 2, which consists of a silicone elastomer and fluorescent particles consisting of $Sr_2P_4O_7:Eu^{2+}$, is fastened to the rear wall 4 in the area of the chamber 5 in order to preferably obtain a desired emission in the range of 400 nm to 500 nm.

A mask 8 is clamped on the front wall 3 in the edge areas 6. This mask 8 is designed as a molded spring steel sheet, which covers the edge areas at least to the extent that the housing 1 is shadowed against radiation reaching the housing 1 in the area of the connection points 7. The molded steel sheet 8 is bent over at the outer edges such that it can clampingly extend around the front wall 3 when it is attached to that wall.

To remove gas bubbles from the chamber 5, a viscoelastic area 9 (plug bonded in place), through which, for example, a syringe can be passed to draw off the gas, is, moreover, provided in the rear wall 4.

FIG. 2 shows a cross-sectional side view of an irradiation arrangement according to the present invention. The housing 1 is largely identical to that shown in FIGS. 1a and 1b. Therefore, identical elements are essentially also designated by the same reference numbers. Reference is made to the corresponding description of the figures.

Contrary to the embodiment shown in FIGS. 1a and 1b, the mask 8 is integrated in the changing bracket 10 in this case. The changing bracket 10 has projections for this purpose in the edge areas of the front wall, the projections shadowing the connection points 7 against the radiation.

The housing 1 is held in the changing bracket 10 together with a UV-emitting radiation source 11. The housing is pushed in for this purpose in guide rails 17 that are open toward the side and can thus be easily replaced. The UV-emitting radiation source 11 is likewise held replaceably in the changing bracket 10, the holding elements provided for this purpose not being shown in FIG. 2. It is indicated only schematically that the radiation source 11 is fastened in the changing bracket 10.

LIST OF REFERENCE NUMBERS

1 Housing of the radiation converter
2 Fluorescent film
3 Front wall of housing 1 with edge projection 3a (FIG. 2)
4 Rear wall of housing 1
5 Liquid chamber
6 Edge areas of front wall 3 and rear wall 4
7 Connection point
8 Mask
9 Viscoelastic area (plug)
10 Changing bracket
11 UV-emitting radiation source

What is claimed is:

1. Radiation converter, for a UV-emitting radiation source, comprising a fluorescent layer,
characterized in that
the said fluorescent layer (2) is arranged in a housing (1), through which the UV radiation emitted by the radiation source can pass, the said housing (1) having
a. a front wall (3) made of a UV-permeable material and
b. a rear wall (4) made of a UV-impermeable material on the side of the said housing (1) located opposite the said front wall (3),
c. wherein a liquid chamber (5) is formed between the said front wall (3) and the said rear wall (4), and
d. the said fluorescent layer (2) is arranged between the said front wall (3) and the said rear wall (4).

2. Radiation converter in accordance with claim 1, characterized in that the said fluorescent layer (2) is in the form of a film.

3. Radiation converter in accordance with claim 1, characterized in that the said fluorescent layer (2) is in contact with the said rear wall (4) and adjoins the said liquid chamber (5).

4. Radiation converter in accordance with claim 1, characterized in that the said fluorescent layer (2) consists of a silicone elastomer with incorporated fluorescent particles.

5. Radiation converter in accordance with claim 4, characterized in that the said fluorescent layer (2) contains different fluorescent particles in different areas.

6. Radiation converter in accordance with claim 4, characterized in that the incorporated fluorescent particles consist of $Sr_2P_2O_7:EU^{2+}$.

7. Radiation converter in accordance with claim 1, characterized in that the silicone elastomer is prepared by free radical addition polymerization.

8. Radiation converter in accordance with claim 1, characterized in that the said front wall (3) and the said rear wall (4) form plane parallel surfaces.

9. Radiation converter in accordance with claim 1, characterized in that the said liquid chamber (5) is filled with at least one cooling liquid.

10. Radiation converter in accordance with claim 9, characterized in that the at least one cooling liquid is selected from the group consisting of silicone oils and water.

11. Radiation converter in accordance with claim 1, characterized in that the said front wall (3) and the said rear wall (4) consist of an acrylate polymer.

12. Radiation converter in accordance with claim 11, characterized in that the acrylate polymer is a homopolymer, copolymer or block polymer of acrylate monomers, selected from the group consisting of alkyl acrylates and alkyl methacrylates.

13. Radiation converter in accordance with claim 1, characterized in that the said front wall (3) and the said rear wall (4) are connected with one another in substance in their edge areas for the liquid-tight sealing of the liquid chamber (5).

14. Radiation converter in accordance with claim 13, characterized in that the connection in substance is a bonding.

15. Radiation converter in accordance with claim 1, characterized in that the said front wall (3) is provided with a said mask (8) in the said edge areas (6) to shadow said connection points (7) of the said two walls.

16. Radiation converter in accordance with claim 1, characterized in that a said viscoelastic area (9) is provided in at least one of the said two walls (3, 4), which said area passes through the entire thickness of the said wall (4).

17. Radiation converter in accordance with claim 1, characterized in that it also has a said changing bracket (10) for the said housing (1).

18. Irradiation arrangement, comprising a said, UV-emitting radiation source (1) and a said fluorescent layer (2), characterized in that the said radiation converter in accordance with claim 1 is arranged in the ray path of the said UV-emitting radiation source (11).

19. Irradiation arrangement in accordance with claim 18, characterized in that the said radiation converter is held in a said changing bracket (10), which is connected with the said UV-emitting radiation source (11).

20. Radiation converter in accordance with claim 5, characterized in that the incorporated fluorescent particles consist of $Sr_2P_2O_7:EU^{2+}$.

* * * * *